US00PP14661P39

(12) United States Plant Patent
Bentley

(10) Patent No.: US PP14,661 P3
(45) Date of Patent: Mar. 30, 2004

(54) *GAURA LINDHEIMERI* PLANT NAMED 'BENSO'

(50) Latin Name: *Gaura lindheimeri*
Varietal Denomination: Benso

(75) Inventor: Howard Bentley, Victoria (AU)

(73) Assignee: Pride of Place Plants (CA)

( * ) Notice: Subject to any disclaimer, the term of this patent is extended or adjusted under 35 U.S.C. 154(b) by 0 days.

(21) Appl. No.: 10/160,976

(22) Filed: May 30, 2002

(65) Prior Publication Data

US 2003/0226184 P1 Dec. 4, 2003

(51) Int. Cl.[7] ..... A01H 5/00
(52) U.S. Cl. ..... Plt./226
(58) Field of Search ..... Plt./226

*Primary Examiner*—Kent Bell
(74) *Attorney, Agent, or Firm*—Christie, Parker & Hale, LLP

(57) ABSTRACT

A new variety of *Gaura lindheimeri* plant named 'Benso' having pale pink flowers produced on a dense plant.

1 Drawing Sheet

Classification:
The present invention relates to a new *Gaura lindheimeri* plant.
Variety denomination:
The new plant has the varietal denomination 'Benso'.

BACKGROUND OF THE INVENTION

The present invention relates to a new and distinct variety of Gaura having pale pink flowers and dense plant habit. The new cultivar is known botanically as *Gaura lindheimeri* and will be referred to hereinafter by the variety name 'Benso'.

Asexual reproduction of the new cultivar was first accomplished using softwood cuttings in a propagation nursery at Wonga Park, Victoria, Australia. Since that time, through successive generations, the characteristics of the new variety have been determined stable and reproduced true to type.

SUMMARY OF THE INVENTION

The following traits in combination distinguish the 'Benso' variety from all other commercial varieties known to the inventor. 'Benso' has not been tested under all possible conditions and phenotypic differences may be observed with variations in environmental, climatic and cultural conditions.

1. *Gaura lindheimeri* 'Benso' exhibits pale pink petal color.
2. *Gaura lindheimeri* 'Benso' exhibits dense plant habit.

COMPARISON WITH PARENT

'Benso' is a naturally occurring branch mutation discovered in a controlled planting of *Gaura lindheimeri* 'Siskiyou Pink' (unpatented).

'Benso' is distinguishable from the parent by its flower color and habit.

In comparison, the plant most similar to 'Benso' is *Gaura lindheimeri* (unpatented). 'Benso' differs from this variety in a more dense habit and pale pink flower color as opposed to *Gaura lindheimeri's* white flowers. In comparison to 'Colso' (co-pending U.S. Plant patent application Ser. No. 10/160,592), of the same parentage, 'Benso' differs in not having variegated foliage and having a pale pink flower color.

'Crimson Butterflies' (U.S. Plant Pat. No. 13,189), although also having the same female parent, has a shorter plant height and darker flower color than 'Benso'.

BRIEF DESCRIPTION OF THE DRAWING

The accompanying illustration depicts plants of the new variety in color as true as possible in color photographic illustrations of this nature.

BOTANICAL DESCRIPTION OF THE PLANT

Figure 1:
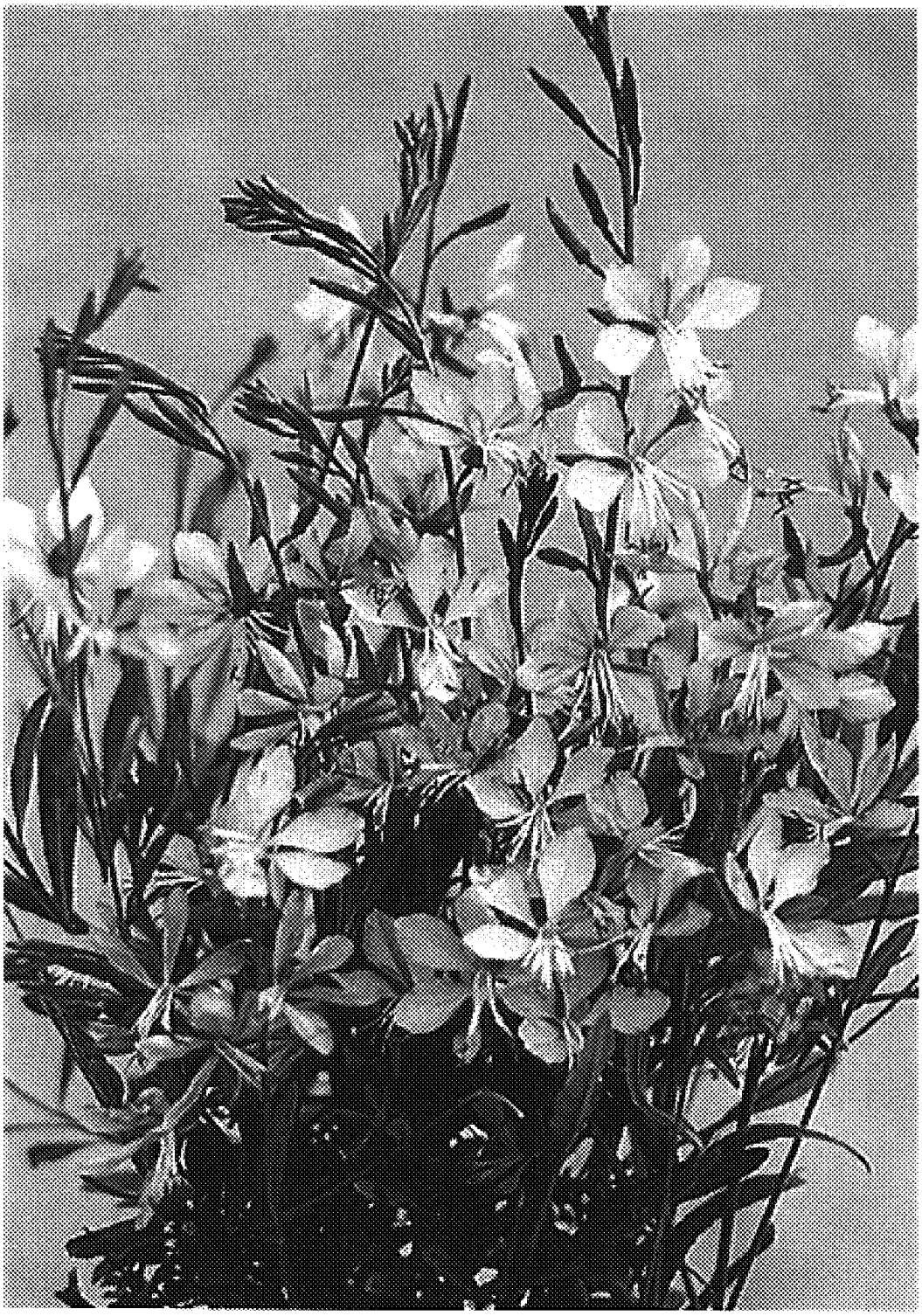
FIG. 1 shows the plant of the new variety.

The following is a description of the new variety 'Benso'. Data was collected from plants grown in outdoor conditions, 9 months of age, in flower, at Wonga Park, Victoria, Australia during the month of April. The color determinations are in accordance with the 1995 Edition of The Royal Horticultural Society Colour Chart ("R.H.S.C."), London, England, except where general color terms of ordinary dictionary significance are used.

The growing requirements are similar to other Gaura.

PLANT DESCRIPTION

Cultural preferences: Plant in full sun or partial shade and fast-draining soil.
Bloom period: Spring and Summer, extending into fall, Wonga Park, Victoria, Australia.
Plant habit: Dense spreading mound.
Height: About 75 cm at maturity.
Width: About 90 cm at maturity.
Hardiness: USDA Zone 5 to 10.
Propagation: Propagation is accomplished using vegetative cuttings.
Time to develop roots: About 10 to 14 days, when rooted on a heated bench.
Crop time: About 12 to 14 weeks to produce a 14 cm container plant size with flower from a rooted cutting.
Disease resistance: Generally disease resistant, susceptible to two-spotted mite.
Stem:
*Shape.*—Cylindrical.
*Color.*—137B to 137C.

*Dimensions.*—About 50 cm in length and about 0.5 cm in diameter (max dimensions).
*Surface.*—Pubescent with whitish hairs up to about 0.5 mm in length.
*Basal stem color.*—Near 199A.
Branching:
*Basal branching.*—Some lateral branching from upper stem nodes once flowering is initiated.
Internode length: About 1.2 to 1.8 cm between nodes.
Branching habit: Basal branching with spreading stems.

FOLIAGE

Shape: Linear to lanceolate.
Division: Simple.
Apex: Acute.
Base: Attenuate.
Venation: Reticulate.
Vein color (adaxial surfaces): Near 146C.
Vein color (abaxial surfaces): Between 146B and 146C.
Margins: Slightly Undulate.
Arrangement: Alternate.
Attachment: Sessile.
Surfaces (adaxial and abaxial): Finely Pubescent to glabrous.
Mature leaf: Dimensions: Mature leaf dimensions range from about 6 to 8 cm in length and about 1.2 to 1.4 cm in width.
Leaf color (adaxial surface): Near 137B. Winter anthocyanin coloration can result in partial to total coloration of near 187A.
Leaf color (abaxial surface): Near 137B.
Petiole: None.
Stipules: None.

FLOWERS

Inflorescence: Raceme.
Dimensions of inflorescence: About 30 cm to 35 cm in length and about 6 cm in diameter (at maturity).
Flower dimensions: About 3 cm in height and about 3 cm in width.
Total number of flowers: About 30 to 40 flowers per raceme.
Persistent or self-cleaning: Self-cleaning.
Aspect: Facing horizontally.
Sexuality: Bisexual.
Bud dimensions: About 0.3 cm in width and about 2.2 to 2.5 cm in length.
Bud shape: Linear.
Bud color: Buds that are completely closed are the color near 179B.
Flower color (adaxial surfaces): Main petal color (interveinal areas) 155C and 56D. Veination color near 55B.
Flower color (abaxial surfaces): Main petal color (interveinal areas) 155C and 56D. Veination color near 55B.
Petals: Two upper and three lower.
*Shape.*—Elliptic.
*Apex.*—Acute.
*Base.*—Cuneate.
*Fused or unfused.*—Unfused.
*Dimensions.*—About 0.9 cm in width and about 1.6 cm in length.
*Margin.*—Entire.
*Surface.*—Glabrous.
Calyx:
*Dimensions.*—About 1.6 cm in length and about 0.5 cm in diameter.
*Surface.*—Pubescent.
Sepals: Four in number.
*Fused or unfused.*—Fused. Partially separate once petals are fully open.
*Surface.*—Pubescent.
Peduncle:
*Dimensions.*—About 10 cm to about 15 cm in length and about 2 mm in width.
*Surface.*—Pubescent.
Flower fragrance: Flowers have no fragrance.

REPRODUCTIVE ORGANS

Stamens: Eight in number.
*Color.*—Near 155C.
*Dimensions.*—About 1.3 cm in length and about 0.50 mm in diameter.
Anther:
*Dimensions.*—About 2.5 mm in length and about 0.5 mm in width.
*Color.*—Near 187A.
*Shape.*—Linear.
Pollen: Present.
*Amount.*—Moderate amount.
*Color.*—Near 10A.
Pistil: One.
*Dimensions.*—About 1.5 cm in length and 0.50 mm in width.
*Color.*—Near 57C.
Ovary:
*Position.*—Inferior.
*Color.*—Near 187A.
*Shape.*—Linear to elliptic.
*Dimensions.*—About 8 mm in length and about 1.5 mm in diameter.
Seed production: Seed production has not been observed to date.

I claim:

1. A new and distinct *Gaura lindheimeri* plant named 'Benso' substantially as shown and described.

* * * * *